(12) United States Patent
Leitner et al.

(10) Patent No.: US 6,525,209 B1
(45) Date of Patent: Feb. 25, 2003

(54) METHOD OF PRODUCING EPOXIDES

(75) Inventors: Walter Leitner, Mülheim an der Ruhr (DE); Frank Loeker, Nottingham (GB)

(73) Assignee: Studiengesellschaft Kohle mbH, Mulhelm an der Ruhr (DE)

( * ) Notice: Subject to any disclaimer, the term of this patent is extended or adjusted under 35 U.S.C. 154(b) by 0 days.

(21) Appl. No.: 09/958,239

(22) PCT Filed: Mar. 28, 2000

(86) PCT No.: PCT/EP00/02719

§ 371 (c)(1),
(2), (4) Date: Oct. 5, 2001

(87) PCT Pub. No.: WO00/61570

PCT Pub. Date: Oct. 19, 2000

(30) Foreign Application Priority Data

Apr. 8, 1999 (DE) .......................... 199 15 903

(51) Int. Cl.⁷ ............................................ C07D 301/06
(52) U.S. Cl. ....................................................... 549/532
(58) Field of Search .......................................... 549/532

(56) References Cited

U.S. PATENT DOCUMENTS 5,210,336 A * 5/1993 Gaffney et al.

FOREIGN PATENT DOCUMENTS

| EP | 540 009 A1 | * | 5/1993 |
| GB | 970 337 | * | 9/1964 |
| GB | 130 2143 | * | 1/1973 |

OTHER PUBLICATIONS

Birnbaum et al., J. Mol. Catal. A: Chem., vol. 139 (1999) pp. 11–24.*

Pesiri et al., Chem. Commun., vol. 9 (1998) pp. 1015–1016.*

Haas et al., Tetrahedron Letters, vol. 39 (1998) pp. 5923–5926.*

* cited by examiner

*Primary Examiner*—T. A. Solola
(74) *Attorney, Agent, or Firm*—Norris McLaughlin & Marcus

(57) ABSTRACT

The present invention relates to the preparation of epoxides by the oxidation of olefins using molecular oxygen with the addition of an aldehyde additive, characterized in that the oxidation is performed in compressed carbon dioxide as the solvent, which, as compared to many conventional organic solvents, is stable towards oxidation, reduces the danger of explosion and is toxicologically and ecologically safe.

13 Claims, No Drawings

METHOD OF PRODUCING EPOXIDES

This application is a 371 of PCT/EP00/02719, filed on Mar. 28, 2000.

The present invention relates to the preparation of epoxides by the oxidation of olefins using molecular oxygen with the addition of an aldehyde additive, characterized in that the oxidation is performed in compressed carbon dioxide as the solvent.

The preparation of epoxides by the oxidation of olefins is a technically important process of great economical significance (cf. Römpp-Chemie Lexikon, Georg Thieme Verlag Stuttgart-New York 1997, 10th edition, Volume 2, 1186). From an ecological and economical point of view, the use of molecular oxygen as the oxidant (in the form of pure oxygen or atmospheric oxygen) is of particular interest. This is achieved, for example, by the addition of aldehyde additives to reaction mixtures consisting of the substrate and a suitable liquid organic solvent, wherein the presence of expensive transition metal catalysts which are difficult to prepare is usually required, however (Bull. Chem. Soc. Jpn. 1995, 68, 17–35, and Chem. Commun. 1997, 69–70).

The oxidation of cyclohexene to form epoxycyclohexane with molecular oxygen with the addition of an aldehyde additive in $CH_2Cl_2$ as the solvent was described with a simple catalyst which can be prepared from iron powder and catalytic amounts of a carboxylic acid (preferably acetic acid) (J. Am. Chem. Soc. 1992, 114, 7913–7914). In the application EP 0 540 009 A1, it is described that a catalyst can even be completely dispensed with under such conditions. However, the use of large amounts of the solvent $CH_2Cl_2$, which is ecologically and toxicologically dangerous, is a considerable drawback of these reactions. Our own examinations (Examples 12 to 15) have shown that $CH_2Cl_2$ in this process cannot be easily replaced by other solvents which are less dangerous, such as toluene, because significantly lower yields and side reactions through oxidation of the solvent result. In addition, the use of many conventional organic solvents requires that the explosion limits of the solvents are taken into account when molecular oxygen serves as the oxidant, which greatly limits the useful range of oxygen partial pressures.

Thus, it has been the object of the present invention to find a suitable solvent for the epoxidation of olefins with molecular oxygen with the addition of an aldehyde additive, wherein the solvent should be stable towards oxidation, reduce the danger of explosion and be toxicologically and ecologically safe.

We have found that compressed (liquid or supercritical) carbon dioxide ideally meets these requirements, and we here describe a method for the preparation of epoxides of general formula II (see below) by the oxidation of olefins of general formula I (see below) using molecular oxygen with the addition of an aldehyde additive of general formula III (see below), characterized in that the oxidation is performed in compressed carbon dioxide as the solvent.

As said olefins, substrates of general formula I can be employed

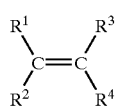

Formula I wherein $R^1$, $R^2$, $R^3$ and $R^4$ may be the same or different, can be independently selected and may comprise a hydrogen atom or straight or branched chain, cyclic or aromatic $C_1$–$C_{20}$ hydrocarbons in which one or more carbons may be replaced by heteroatoms or/and which may be substituted with halogen, hydroxy, alkoxy, phenoxy, acyloxy, acyl, alkoxycarbonyl or phenoxycarbonyl groups, wherein the residues $R^1$, $R^2$, $R^3$ or $R^4$ may be interconnected to form rings or fused ring systems. In the method developed by us, the olefins of general formula I are oxidized to yield the corresponding epoxides of general formula II

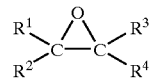

Formula II wherein $R^1$, $R^2$, $R^3$ and $R^4$ are defined as for formula I. This is effected with the addition of an aldehyde additive of general formula III

Formula III wherein $R^5$ may be a hydrogen atom, a $C_1$–$C_{10}$ alkyl group, a halogen-substituted $C_1$–$C_{10}$ alkyl group, an aryl group, a halogen-substituted aryl group, an arylalkyl group or a halogen-substituted arylalkyl group.

In the present invention, compressed, preferably supercritical, carbon dioxide ($scCO_2$, critical data: $T_c$=30.9° C., $p_c$=73.75 bar, $\rho_c$=0.468 g·cm$^{-3}$) serves as the solvent. The total pressure is within a range of from 40 to 500 bar, preferably from 60 to 200 bar.

The reaction temperature is within a range of from 0 to 200° C., preferably between 31° C. and 100° C. The reaction time is not generally limited and depends on the course of the reaction, which can be monitored by means of suitable analytical methods (e.g., GC, NMR, IR). The reaction time is usually within a range of from 1 to 48 hours.

The quantity of aldehyde employed is not particularly limited, but is usually from 0.1 to 30 mol, preferably from 1 to 10 mol, per mole of olefin.

The quantity of olefin employed is not particularly limited, but is usually from 0.1 to 50 mmol per 100 g of $CO_2$, preferably from 0.5 to 10 mmol per 100 g of $CO_2$.

Attention must be paid to the fact that the danger of explosion upon addition of oxygen increases as the amount of olefin increases.

The molecular oxygen can be added in a pure form or in the form of mixtures with other gases (e.g., as atmospheric oxygen). The partial pressure of the oxygen employed is not particularly limited, but is usually from 1 to 20 bar, preferably from 1 to 5 bar. The use of compressed $CO_2$ as the solvent as described herein has the advantage, as compared to many conventional organic solvents, that $CO_2$ as a solvent is stable towards oxidation and reduces the danger of explosion. Therefore, after dissolving the olefin and aldehyde in the amount of $CO_2$ needed as a solvent, higher partial pressures of oxygen can be safely employed, in contrast to many conventional organic solvents.

The method described by us is also compatible with the use of known oxidation catalysts. Such catalysts may serve to increase the reaction rate or enhance selectivity. The catalysts may be employed in a solid or liquid form or in a form dissolved in the reaction medium. Typical catalysts are described in detail in Bull. Chem. Soc. Jpn. 1995, 68, 17–35, and EP 0 540 009 A1, but the method is not limited to the catalysts mentioned there.

Further, due to the fact that the solvent properties of supercritical carbon dioxide vary with pressure and temperature, a separation of the main products (epoxide) and by-products (carboxylic acid of the aldehyde additive, further oxidation products of the olefin) and unreacted educts (olefin and aldehyde) from the reaction mixture is possible when the external parameters are selected appropriately. Known methods in which $scCO_2$ is used for material separation are described in Angew. Chem. Int. Ed. EngI. 1978, 17, 702, and in M. McHugh, V. Krukonis, Supercritical Fluid Extraction, Butterworth Publishers, 1986. When a catalyst is additionally employed, its separation is also possible.

The present invention shall be further described by the following selected Examples, without intending to limit the application of the method in any way by the Examples chosen.

EMAMPLES 1–4 cis-Cyclooctene (2.50 mmol) was added to a 100 ml steel autoclave together with the additive isobutyraldehyde in a molar ratio of C/I, and $CO_2$ was introduced using a compressor to a density ($\rho(CO_2)$=weight of charged $CO_2$/reactor volume) of 0.75 g·cm$^{-3}$. Subsequently, the pressure in the autoclave was increased with molecular oxygen to such an extent that the $O_2$ quantity corresponded to the desired partial pressure of 3 bar. The autoclave was heated up to the reaction temperature T, and after the reaction time t, the composition of the product was analyzed by GC. The product distribution was established by integrating the peak areas in the gas chromatogram. The GC factor of epoxycyclooctane was determined by a calibration measurement. The identification of the oxidation products was effected by GC/MS analysis. The results of the reactions are summarized in Table 1.

TABLE 1-continued

| Example No. | C/I | T (° C.) | t (h) | Conversion (%)[a] | Selectivity (%)[b] |
|---|---|---|---|---|---|
| 3 | 1:1 | 55–56 | 18 | 2 | >95 |
| 4 | 1:2 | 25–28[c] | 18 | 14 | >99 |

[a]based on cis-cyclooctene
[b]selectivity = (GC proportional area of epoxycyclooctane)/(GC proportional area of all detected oxidation products of the olefin). Oxidation products having a proportional area of less than 0.2% were neglected.
[c]in liquid $CO_2$

EXAMPLE 5 cis-Cyclooctene (2.50 mmol) was added together with the additive isobutyraldehyde (5.00 mmol) under an oxygen atmosphere in a 100 ml steel autoclave, and $CO_2$ was introduced using a compressor to a density ($\rho(CO_2)$=weight of charged $CO_2$/reactor volume) of 0.75 g cm$^{-3}$. The autoclave was heated up to a reaction temperature of 55–56° C. and after a reaction time of 18 hours the product composition was analyzed according to Examples 1–4. Conversion of cis-cylooctene was 94% with a selectivity for epoxycyclooctane of >99%.

EXAMPLES 6–10

The olefin (2.50 mmol) was added together with the additive isobutyraldehyde 500 mmol) to a steel autoclave, and $CO_2$ was introduced using a compressor to a sity ($\rho(CO_2)$=weight of charged $CO_2$/ reactor volume) of 0.75 g·cm$^{-3}$. Subsequently, the pressure in the autoclave was increased with molecular oxygen to such an extent that the $O_2$ quantity corresponded to the desired partial pressure of 3 bar. The autoclave was heated up to a reaction temperature of 55–56° C., and after a reaction time of 18 hours, the composition of the product was analyzed by GC. The product distribution was established by integrating the uncorrected peak areas in the gas chromatogram. The identification of the oxidation products was effected by GC/MS analysis. The results of the reactions are summarized in Table 2.

TABLE 2

| Example No. | Olefin | Conversion (%)[a] | Epoxides | Selectivity (%)[b] |
|---|---|---|---|---|
| 6 | cyclohexene | >99 | epoxycyclohexane | 85 |
|   |   |   | 2,3-epoxycyclohexane-1-one | 6 |
| 7 | trans-3-hexene | 96 | 3,4-epoxyhexane | >98 |
| 8 | (R)-(+)-limonene | 51 | cis-1,2-epoxy-(R)-(+)-limonene | 60 |
|   |   |   | trans-1,2-epoxy-(R)-(+)-limonene | 31 |
|   |   |   | 8,9-epoxy-(R)-(+)-limonene[c] | 9 |
| 9 | 1-octene | 36 | 1,2-epoxyoctane | 87 |
|   |   |   | 3,4-epoxyoctane | 5 |
| 10 | isophorone | 16 | epoxyisophorone | 30 |

[a]based on the olefin
[b]selectivity = (GC proportional area of the epoxide)/(GC proportional area of all detected oxidation products of the olefin). Oxidation products having a proportional area of less than 0.2% were neglected.
[c]2 isomers. The configurations could not be assigned using GC/MS analysis.

TABLE 1

| Example No. | C/I | T (° C.) | t (h) | Conversion (%)[a] | Selectivity (%)[b] |
|---|---|---|---|---|---|
| 1 | 1:2 | 55–56 | 18 | >99 | >99 |
| 2 | 1:2 | 55–56 | 8 | 90 | >99 |

EXAMPLE 11

Into a 100 ml steel autoclave, 750 μl (8.22 mmol) of isobutyraldehyde was charged under a propene atmosphere (100 ml=4.10 mmol), and $CO_2$ was added using a compressor to a density ($\rho(CO_2)$=weight of charged $CO_2$/reactor volume) of 0.75 g·cm$^{-3}$. Subsequently, the pressure in the autoclave was increased with molecular oxygen to such an extent that the $O_2$ quantity corresponded to the desired partial pressure of 5 bar. The autoclave was heated up to a reaction temperature of 55–56° C., and after a reaction time of 18 hours, the pressure was released through a cooling trap filled with absolute toluene with a glass frit insert at −50° C. The reactor was rinsed with absolute toluene, and the toluene solutions were combined. The composition of the product was analyzed by GC. The product distribution was established by integrating the corrected peak areas in the gas chromatogram. The identification of the oxidation products was effected by GC/MS analysis. To determine the yields of oxidation products, n-heptane was used as an internal standard. The conversion of propene was >73% with a selectivity towards epoxypropane of 14%.

EXAMPLES 12 to 15

Into a 100 ml steel autoclave, 70 ml of absolute toluene was charged. The olefin (2.50 mmol) was added under argon together with the additive isobutyraldehyde (5.00 mmol), and the gas space of the autoclave was purged with molecular oxygen. A gas burette filled with oxygen was connected to the lid of the autoclave. Stirring was performed at 850 rpm at a reaction temperature of 55–56° C. for 18 hours. After cooling to room temperature, the reaction solution was analyzed by GC. The product distribution was established by integrating the corrected peak areas in the gas chromatogram. The peak area of epoxycyclooctane was standardized by calibration measurements, while all other data are uncorrected. The identification of the oxidation products was effected by GC/MS analysis. The results of the reactions are summarized in Table 3. Under otherwise identical conditions, the conversions are always below those achieved in $CO_2$ as the solvent. Further, in addition to the stated reaction products, oxidation products of toluene (benzaldehyde, benzyl alcohol, benzyl hydroperoxide, benzoic acid) were detected in all reactions performed in toluene.

TABLE 3

| Example No. | Olefin | Conversion (%)[a] | Epoxides | Selectivity (%)[b] |
|---|---|---|---|---|
| 12 | cis-cyclooctene | 84 | epoxycyclooctane | >99 |
| 13 | trans-3-hexene | 69 | 3,4-epoxyhexane | >98 |
| 14 | 1-octene | 23 | 1,2-epoxyoctane | 67 |
|  |  |  | 3,4-epoxyoctane | 7 |
| 15 | isophorone | 4 | epoxyisophorone | 18 |

[a]based on the olefin
[b]selectivity = (GC proportional area of the epoxide)/(GC proportional area of all detected oxidation products of the olefin). Oxidation products having a proportional area of less than 0.2% were neglected.

What is claimed is:

1. A method for the preparation of epoxides comprising the oxidation of olefins using molecular oxygen with the addition of aldehyde additives, characterized in that the oxidation is performed in compressed carbon dioxide as the solvent.

2. The method according to claim 1, characterized in that compounds of general formula I

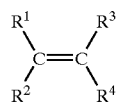

Formula I are employed as said olefins wherein $R^1$, $R^2$, $R^3$ and $R^4$ may be the same or different, can be independently selected and represent a hydrogen atom or straight or branched chain, cyclic or aromatic $C_1$–$C_{20}$ hydrocarbons in which one or more carbons may be replaced by heteroatoms or/and which may be substituted with halogen, hydroxy, alkoxy, phenoxy, acyloxy, acyl, alkoxycarbonyl or phenoxycarbonyl groups, wherein the residues $R^1$, $R^2$, $R^3$ or $R^4$ may be interconnected to form rings or fused ring systems.

3. The method according to claim 1, characterized in that compounds of general formula III

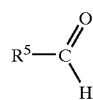

Formula III are employed as said aldehyde additive wherein $R^5$ is a hydrogen atom, a $C_1$–$C_{10}$ alkyl group, a halogen-substituted $C_1$–$C_{10}$ alkyl group, an aryl group, a halogen-substituted aryl group, an arylalkyl group or a halogen-substituted arylalkyl group.

4. The method according to claim 1, characterized in that the total pressure during the reaction is within a range of from 40 to 500 bar, preferably from 60 to 200 bar.

5. The method according to claim 1, characterized in that the reaction temperature is within a range of from 0 to 200° C., preferably from 31 to 100° C.

6. The method according to claim 4, wherein said compressed carbon dioxide is in a supercritical state.

7. The method according to claim 1, characterized in that the partial pressure of the molecular oxygen is within a range of from 1 to 20 bar, preferably from 1 to 5 bar.

8. The method according to claim 7, wherein said molecular oxygen is employed in the form of pure oxygen.

9. The method according to claim 7, wherein said molecular oxygen is employed in the form of admixtures with other gases.

10. The method according to claim 9, wherein said molecular oxygen is employed in the form of atmospheric oxygen.

11. The method according to claim 1, characterized in that an oxidation catalyst, which may be liquid, solid or dissolved in the reaction mixture and which is otherwise known, is employed to increase the reaction rate or enhance selectivity in the epoxidation.

12. The method according to claim 1, characterized in that the reaction mixture is processed by a material separation in compressed $CO_2$.

13. The method according to claim 12, wherein said reaction and material separation are combined in one integrated process.

* * * * *